United States Patent [19]

McNeal et al.

[11] Patent Number: 4,653,124
[45] Date of Patent: Mar. 31, 1987

[54] FACE MASK HAVING AN AIR DUCT CONNECTABLE TO A GOGGLE

[75] Inventors: Joseph R. McNeal, Hailey; David Robrahn, Ketchum, both of Id.

[73] Assignee: Scott USA, Sun Valley, Id.

[21] Appl. No.: 755,456

[22] Filed: Jul. 16, 1985

[51] Int. Cl.⁴ ............................................... A61F 9/02
[52] U.S. Cl. .............................................. 2/427; 2/9;
2/436; 128/206.21
[58] Field of Search ................... 2/427, 428, 429, 430,
2/431, 434, 436, 437, 9; 128/206, 207.13,
206.23, 201.15, 206.21

[56] References Cited

U.S. PATENT DOCUMENTS

| | | |
|---|---|---|
| 1,686,113 | 10/1928 | Tillyer . |
| 1,916,630 | 5/1930 | Moran et al. . |
| 1,942,394 | 1/1934 | Baker . |
| 1,947,137 | 2/1934 | Fraser . |
| 2,435,653 | 2/1948 | Maurer .......................... 128/207.13 |
| 2,665,686 | 3/1952 | Wood et al. . |
| 2,903,700 | 9/1959 | Finken et al. ....................... 2/427 X |
| 3,152,588 | 10/1964 | Rogowski . |
| 3,274,614 | 9/1966 | Boyer ..................................... 2/427 |
| 3,298,031 | 1/1967 | Morgan .............................. 2/427 X |
| 3,822,698 | 7/1974 | Guy . |
| 3,825,953 | 7/1974 | Hunter . |
| 3,838,466 | 10/1974 | Poirier . |
| 3,945,044 | 3/1976 | McGee et al. . |
| 3,971,368 | 7/1976 | Forbes et al. ................... 128/201.15 |
| 4,011,595 | 3/1977 | Shields . |
| 4,178,742 | 12/1979 | Longfellow . |
| 4,250,577 | 2/1981 | Smith . |
| 4,435,852 | 3/1984 | Nesler . |

FOREIGN PATENT DOCUMENTS 453071 11/1948 Canada ..................................... 2/436
150848 9/1981 Fed. Rep. of Germany .

Primary Examiner—Werner H. Schroeder
Assistant Examiner—Andrew M. Falik
Attorney, Agent, or Firm—Jenner & Block

[57] ABSTRACT

A releasably attachable face mask that forms a contiguous channel with an attached goggle to improve goggle ventilation. An elongated pocket or duct formed between two surfaces on the face mask mates with the goggle ventilation system to form the contiguous channel. The channel forms a venturi to draw air out from the goggle interior to the atmosphere through the contiguous channel.

15 Claims, 8 Drawing Figures

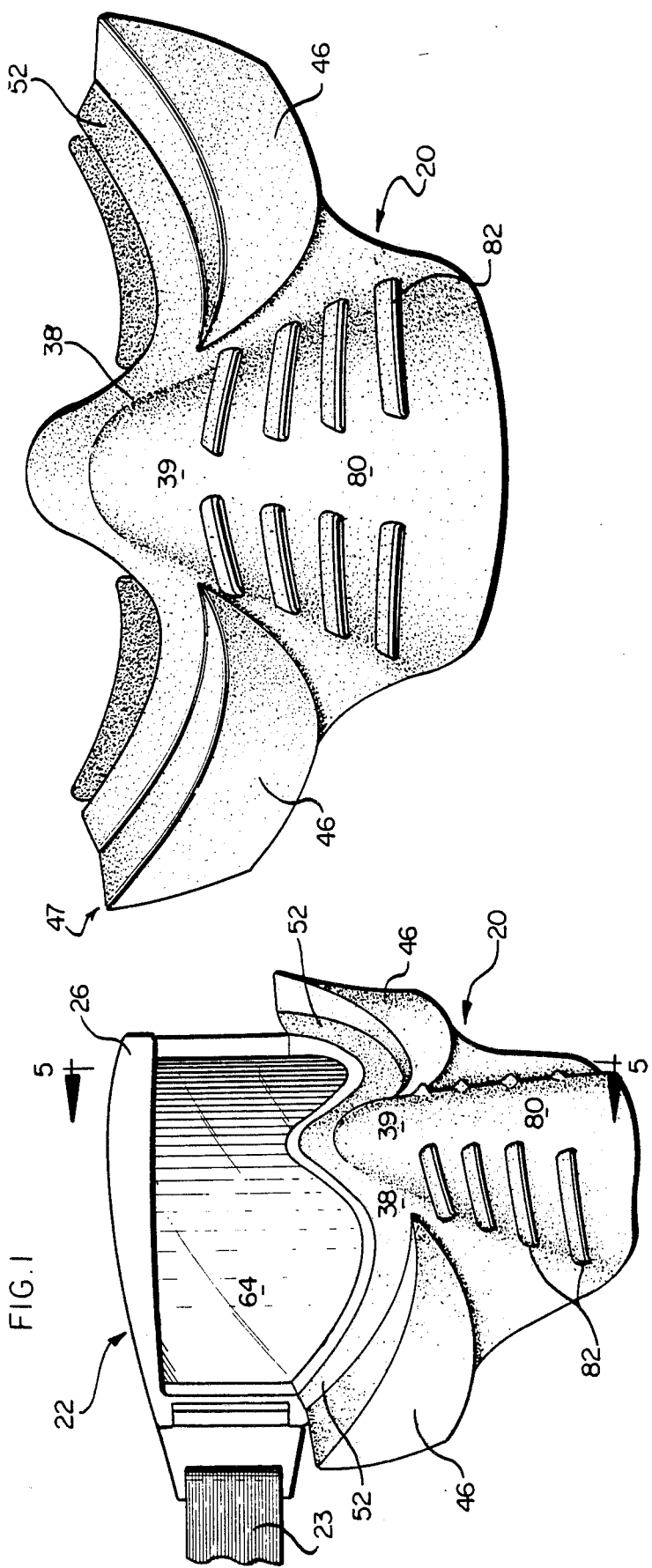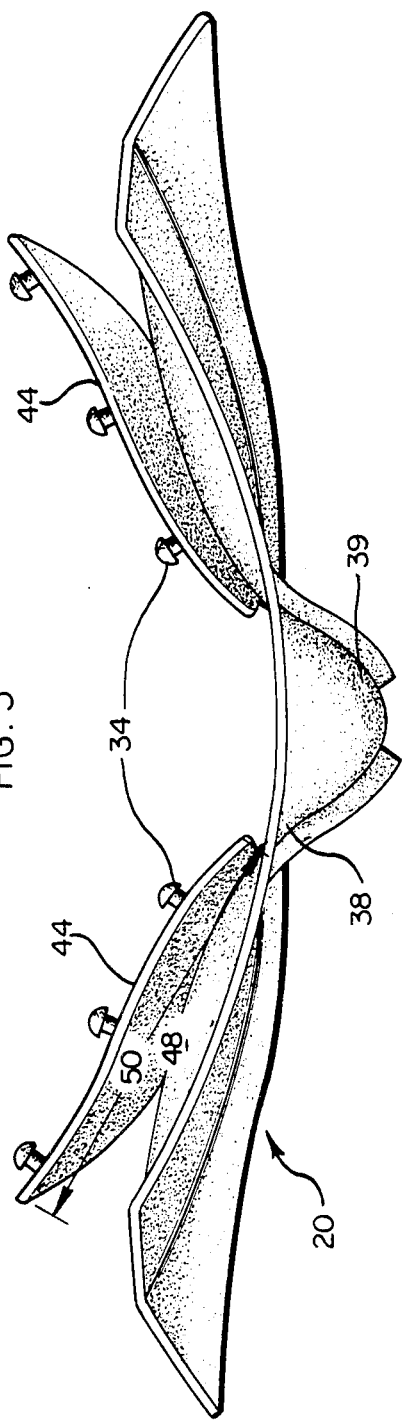

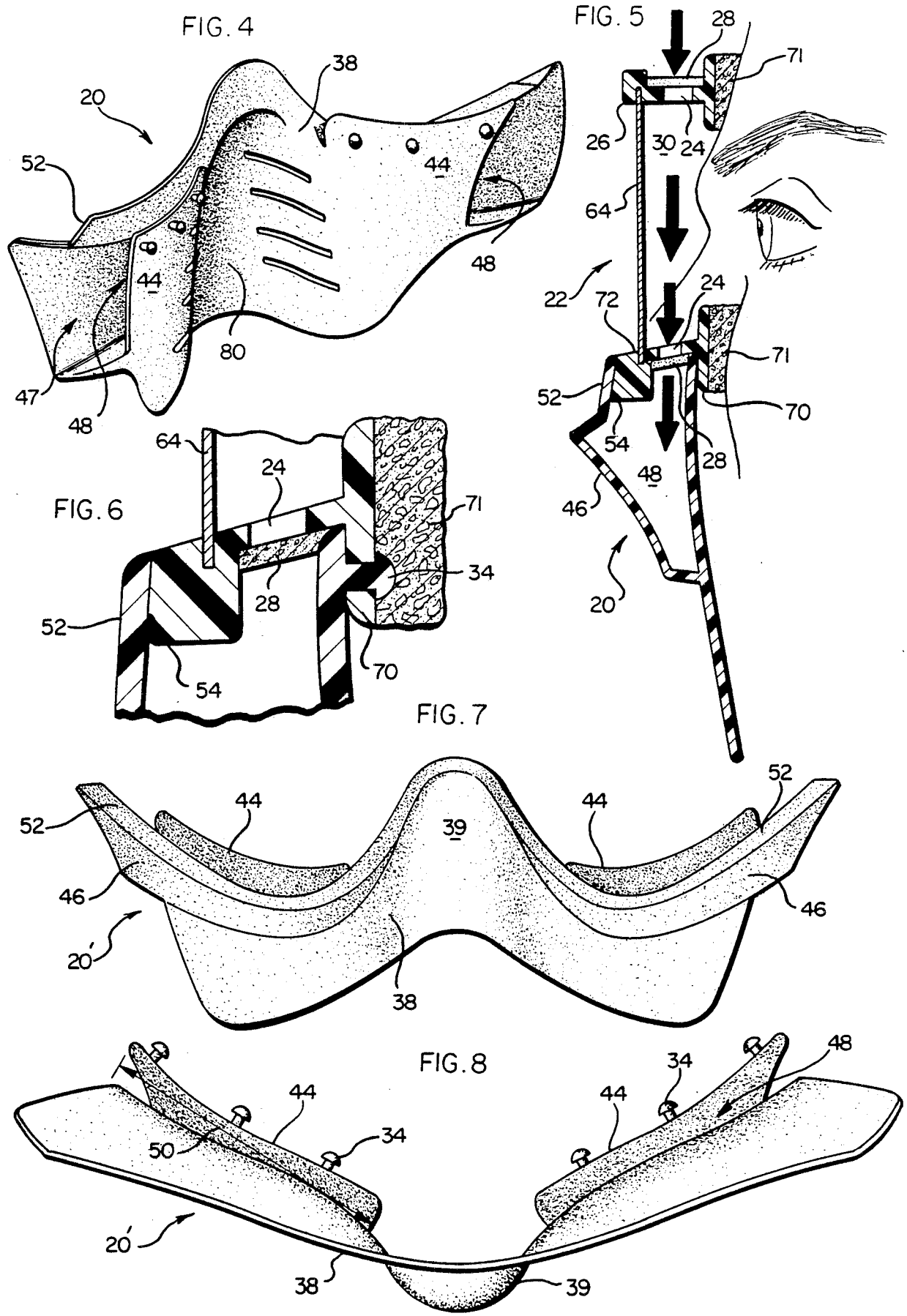

FACE MASK HAVING AN AIR DUCT CONNECTABLE TO A GOGGLE

BACKGROUND OF THE INVENTION

This invention relates to a face mask that attaches to a goggle and cooperates therewith to improve ventilation and reduce fogging. The face mask has an air channel or duct which mates with the goggle ventilation system to move moist air out and away from the wearer's face, and thus reduce goggle fogging.

Goggles are used in many activities, such as motorcycle racing, skiing and the like where safety requires the protection of the wearer's eyes from fast moving air, rocks and other foreign matter. Many of these activities, such as motorcycle racing, are conducted in harsh environments and therefore a need exists to protect not only the eyes but the face of a wearer. Thus it has been common to provide a full or partial face mask which detachably connects, when needed, to a goggle.

The use of goggles to protect a wearer's eyes results in air being trapped between the goggle lens and the wearer's face. This interior area, generally referred to hereafter as a goggle cavity, eventually becomes filled with moisture laden air. The moisture in the air then condenses on the lens of the goggle and produces fogging. It is known in the art that apertures formed in the goggle frame to vent air from the goggle cavity will decrease goggle fogging. Apertures are generally formed in at least the top and bottom portion of the frame to allow venting of the air from the goggle cavity. The apertures are typically covered by a porous foam to produce a controlled air exchange while forming a partial barrier to dust, snow and the like.

When face masks have been attached to goggles, their air flow patterns have disrupted the air flow ventilation scheme of the goggles and have tended to aggravate the fogging problem. Some face masks attach to the forward portion of the bottom goggle frame and thus block off the goggle venting system at the bottom of the frame. Other face masks are known, such as shown in U.S. Pat. No. 3,945,044 of McGee, et al. and assigned to the assignee of the present application, in which the face mask attaches at the rear of the lower goggle frame, behind the air vent system, to force the exterior air up into the goggle interior. While this is a form of cooperating face mask and goggle, too much air can be forced into the goggle cavity, and there is no true cooperation between the ventilating system of the face mask and the ventilating system of the goggle.

It also has been known to provide a venturi effect on a face mask so as to aid in drawing moisture laden air away from the nose and mouth region and into the atmosphere so as to attempt to minimize the fogging problem. These approaches achieve various degrees of success depending on the air flow patterns and atmospheric conditions in existence at the time.

Other methods, such as a full face shield that forms an integral part of a helmet have been developed to reduce the fogging problem. This method lacks flexibility as the eye and face protection are combined in one piece, and requires the use of a helmet.

One object of the present invention is to provide a face mask having an air channel that cooperates with the ventilation system of the goggle to which it is attached and works in cooperation therewith to improve ventilation and minimize the problem of fogging.

Another object of the present invention is to provide a face mask in which an air passage channel mates with the ventilation system of the goggle so that the ventilation system of the face mask works with the ventilation system of the goggle and not independently thereof.

Still another object of the present invention is to provide a releasably attachable face mask having a ventilation system in which a venturi system for exhausting air complements the ventilation system of the goggle.

SUMMARY OF THE PRESENT INVENTION

This invention provides a face mask which overcomes the previously discussed disadvantages and achieves the above mentioned objectives.

The present face mask forms an air flow channel in the top portion of the face mask and located to mate with the ventilation system of the goggle to form a contiguous channel. The face mask is further designed such that venturi action on the face mask actively draws air out of the contiguous channel which results in a more efficient exchange of moist air between the goggle cavity and the channel. The face mask becomes an integral part of the ventilation system for the goggle itself and cooperates therewith rather than acting essentially independent of the goggle ventilation system.

A better understanding of the present invention along with other objects and advantages of the invention will become apparent upon reading the following detailed description and upon reference to the drawings. Throughout the drawings, like reference numerals refer to like parts. While illustrative embodiments of the invention are shown in the drawings and will be described in detail herein, the invention is susceptible of embodiment in many different forms and it should be understood that the present disclosure is to be considered as an exemplification of the principles of the invention and is not intended to limit the invention to the embodiments illustrated.

BRIEF DESCRIPTION OF THE DRAWINGS

FIG. 1 is a perspective view of one embodiment of a novel face mask attached to a goggle;

FIG. 2 is a front plan view of the face mask;

FIG. 3 is a top plan view of the face mask;

FIG. 4 is a rear perspective view of the face mask;

FIG. 5 is a cross-sectional view taken substantially along lines 5—5 of FIG. 1;

FIG. 6 is an enlarged fragmentary cross-sectional view showing the face mask and goggle connector system;

FIG. 7 is a front plan view of another embodiment of the face mask suitable for use when the user is wearing a helmet; and FIG. 8 is a top plan view of the embodiment of the face mask shown in FIG. 7.

DESCRIPTION OF THE PREFERRED EMBODIMENTS

Turning to the drawings, a first embodiment of a novel face mask 20 is shown in FIGS. 1-6 which is attachable to a goggle 22. As seen in FIGS. 1, 5 and 6, the goggle 22 may be of standard design such as shown in U.S. Pat. No. 3,945,044 of McGee, et al., owned by the assignee of the present application, the disclosure of the goggle shown therein being hereby incorporated by reference herein. The goggle 22 includes an elastic strap 23, FIG. 1, which attaches to both sides of the goggle. As illustrated in FIG. 5, air flow ventilating apertures 24 are formed around a goggle frame 26 and are covered by a porous foam 28 to allow a slow and controlled exchange of air between the goggle interior 30 adjacent the wearer's eyes and the external environment. The frame has an outside portion 72, see FIG. 5, containing a slot for holding a lens 64 therein. The lens 64 is removable, and can be a single lens 64 as illustrated or a thermal double lens with a sealed interior for cold weather. The inside portion 70 of the goggle frame mounts a soft closed cell foam strip 71 which encircles the wearer's face to cushion the goggle against the face.

The goggle 22 has a connector system, explained particularly with reference to FIG. 6 herein. Snap-in connectors 34 on the face mask 20 are received within spaced apertures located on each side of the lower inside portion 70 of the goggle frame 26. Each connector 34 consists of a post having an enlarged head. The goggle frame 26, formed of injection molded plastic, is somewhat resilient and allows the head to be pushed or snapped through the aperture hole to thereby form a detachable connector system. The foam strip 71 prevents the connector head from contacting the wearer's face. However, other types of connector systems for detachably connecting a face mask 20 to a goggle 22 can be substituted for the present system so long as the face mask 20 can be removed from the goggle frame 26 whenever desired so that the goggle 22 can be used by itself. When conditions warrant the wearing of the face mask 20, such as in motorcycle racing and the like where small pebbles, rocks, mud and other foreign matter may be hurled toward the wearer's face, the face mask 20 can be securely attached to the goggle 22.

The novel face mask 20 consists of a plastic protective member 38 arranged to cover a portion of a wearer's face. Protective member 38 may be formed of injection molded plastic and composed of a single piece, or can be formed of several pieces which are secured together. The member includes a nose portion 39 located to cover the bridge of the wearer's nose. As seen best in FIGS. 2, 3 and 4, a pair of side walls 44 or flaps extend integrally outward and to the side from the nose portion 39. Extending in front of and spaced from the side walls are a pair of side flanges 46 which extend outwardly and away from the nose portion 39. Each flange 46 is spaced away from the rear wall 44 so as to form a duct or pocket 48 therebetween, see FIGS. 5 and 6. The side end of each pocket 48 is open to the atmosphere and forms a side port 47 which allows air flow therethrough as will be explained. The top of the duct pocket defines an elongated opening 50 which is formed by the distal upper end of the side flange 46 and the upper end of the wall 44. The elongated opening mates with the lower portion of the goggle ventilation system, as will be explained, to allow air exchange through the elongated opening and into the pocket 48.

The pair of side flanges 46 have upper distal ends which form a lip or shoulder 52 extending across the length of the wall 44 and spaced therefrom. When the snap-in connectors 34 are inserted into the goggle connector system so as to attach the face mask to the goggle, the shoulder 52 continuously contacts the forward surface of the lower goggle frame 54 so as to form a seal or seat thereagainst which closes the entire elongated top opening 50. Thus, the pocket 48 mates with the lower portion of the frame ventilation system so as to create an air duct.

As seen in FIG. 5, air flows from the goggle interior 30 and through the goggle vents 24 and foam 28 into the pocket or duct channel 48. When the face mask is attached to the goggle frame, the air flow ventilation system of the face mask becomes, in essence, an integral part of the air flow ventilation system of the goggle.

The pair of air channels formed by the side pockets produce venturi forces that act to exhaust air in a direction from the goggle interior into the pockets and out of the side ports 47 of the face mask. Frontal air striking the face mask deflects to the sides and bottom and creates an air flow which serves to carry along the air within the side pockets and thus create the venturi effect. This effect is enhanced by continuously increasing the cross-sectional area of the pair of pockets 48 by expanding the cross-sectional area from the section nearest the nose towards the sides of the mask.

Because the venturi acts to exhaust air within the goggle through the bottom of the goggle ventilation system and out through the pair of side pockets of the face mask, exterior air will enter the goggle at the top or upper ventilation system as seen in FIG. 5. This causes exterior air to be drawn downwardly through the goggle interior, past the eyes of the wearer, and out the bottom of the goggle. It has been found that this air flow pattern is preferable to air flowing upward or in other directions within the goggle interior and aids in reducing fogging.

The protective member 38 extends from the bridge of the wearer's nose downwardly to define a mouth guard 80 which substantially covers a wearer's mouth. The mouth guard 80 further extends laterally outward on either side of the wearer's nose and mouth to substantially cover the wearer's cheeks. An array of open louvers 82 are formed in the mouth portion 80 to allow air to be expelled from the wearer's nose and mouth and be transmitted to the atmosphere. This prevents air from being trapped behind the wearer'mask 20 which reduces the chance of such air entering the goggle interior 30.

Turning to FIGS. 7 and 8, another embodiment of a novel face mask 20' is shown. This embodiment differs primarily in that the protective member 38 forms a partial face shield which extends only to substantially cover a wearer's nose and a reduced portion of the wearer's side cheeks. The rear walls 44 and front flanges 46 of FIGS. 7 and 8 attach to the goggle frame 26 as described previously in reference to FIG. 6. The contiguous channels 50 formed between the face mask 20 and the goggle 22 cooperate to exchange air between the goggle interior and the atmosphere. Ths side portions of the mask 20 have been reduced in size and the mouth guard eliminated to allow the mask 20' to be worn with a helmet. In other respects the face mask 20' has the same novel features of face mask 20.

What is claimed is:

1. A face mask releasably connectable to a goggle in which the goggle has at least one goggle vent for circulating air in a goggle interior, comprising:

a protective member for covering at least a portion of a wearer's face including a central nose portion which forms a passageway for directing air away from the wearer's nose and a first surface and a second surface spaced from the first surface to form therebetween a channel separate from the passageway and which ends in an opening to the atmosphere, and attachment means releasably attaching the protective member to the goggle for aligning the channel of the face mask with the goggle vent to exchange air through the goggle interior and the channel to the atmosphere by venturi action.

2. The face mask of claim 1 wherein said second surface is a flange extending away from said first surface and terminating in a shoulder, said attachment means further aligns the shoulder against the goggle to form a seal which contains air flow within a section of the channel.

3. A face mask releasably attachable to a goggle in which the goggle has a frame and a goggle interior with at least one vent for exchanging air between the interior and the atmosphere, comprising:
   a protective member separate from the goggle for covering at least a portion of a wearer's face including
   a wall having an elongated section,
   a flange spaced from the wall along the elongated section to define therebetween an elongated open pocket terminating in a port open to the atmosphere,
   the wall having attachment means releasably connectable to the goggle frame for mating the flange against the goggle frame with the open pocket in alignment with the vent of the goggle to allow air flow between the goggle interior and the port through the face mask.

4. The face mask of claim 3 wherein a distal end of the flange forms a shoulder member which seats against the goggle frame to seal the elongated open pocket to the vent of the goggle.

5. The face mask of claim 3 wherein the flange and wall tapers outwardly from a junction near the central portion of the protective member to increase the cross sectional area of the elongated pocket in the direction of the port.

6. The face mask of claim 3 for a goggle in which the goggle frame has a rear section adjacent the face of a wearer and a forward section for holding a lens, the vent being formed between the forward section and rear section of the goggle, and connection means located on one of the sections of the goggle frame for engagement with the attachment means of the face mask, wherein the attachment means aligns the flange against the other of the sections of the goggle frame.

7. The face mask of claim 6 wherein the attachment means is formed by a plurality of posts having enlarged heads, and the connection means is formed by a plurality of apertures which receive the elongated posts to form a snap in connector system.

8. The face mask of claim 3 wherein the protective member deflects air striking the face mask past the open port of the elongated pocket to thereby create venturi action which exhausts air from the goggle interior through the elongated pocket to exit at the port.

9. A face mask attachable to a goggle in which the goggle has a frame and a goggle interior with at least one vent for exchanging air between the interior and the atmosphere, comprising:
   a protective member for covering at least a portion of a wearer's face including
   a mouthguard to substantially cover a wearer's mouth region,
   a wall and a flange spaced from the wall to define therebetween a pocket having a first opening and a second opening forming a port open to the atmosphere,
   the wall having attachment means connectable to the goggle frame for mating the flange against the goggle frame with the first opening in alignment with the vent to allow air flow between the goggle interior and the second opening, and
   ventilation means separate from the pocket for allowing air exchange between the wearer's mouth and the exterior.

10. The face mask of claim 9 wherein the ventilation means for the mouth guard comprises a plurality of louvers which extend over and partially cover slots formed in the mouth guard.

11. A combined face mask and goggle which provides for air flow through the goggle and at least a portion of the face mask, comprising:
    a goggle which includes a frame having vent means for permitting air to flow through the goggle interior,
    a face mask, separate from the goggle, which includes a protective member for covering at least a portion of the wearer's face, said member having a central nose portion forming a passageway for directing air away from the wearer's nose and first and second surfaces which extend from the central nose portion of the protective member to the side thereof, and
    attachment means for releasably connecting the face mask to the goggle with the first and second surfaces being aligned on opposite sides of said vent means to channel air independent of the passageway through the spaced surfaces and thereby exchange air from the goggle interior through the face mask.

12. The combined face mask and goggle of claim 11 wherein the protective member deflects air which strikes the surface of the face mask across an opening between the first and second surfaces to create venturi action.

13. The combined face mask and goggle of claim 12 wherein the first and second surfaces diverge outwardly from a junction near the central nose portion of the face mask to define a channel separate from the nose passageway in which the cross sectional area of the channel increases from the junction to the opening in order to enhance the venturi effect.

14. A face mask releasably connectable to a goggle having a pair of goggle vents located in a bottom section of the goggle frame for exhausting air from the goggle interior, comprising:
    a protective member including a central nose portion which forms a nose channel for directing air away from the wearer's nose and a pair of side portions for covering at least a portion of a wearer's face, each side portion including a duct open along its top surface and side surface to form a side channel unconnected with the nose channel, and
    attachment means releasably connecting the protective member to the goggle frame for mating the top surface of each duct with an associated one of the pair of goggle vents to thereby exchange air between the goggle interior and the duct side surfaces of the protective member without intermixing with the air from the wearer's nose.

15. The face mask of claim 14 wherein each duct is formed by a wall and a flange extending away from the wall to form a continuous opening along the top and side surfaces of the duct, and the attachment means releasably seats the wall and flange of each duct on opposite sides of the associated goggle vent.

* * * * *